United States Patent
Bhat et al.

(10) Patent No.: US 9,296,764 B2
(45) Date of Patent: Mar. 29, 2016

(54) HYDROPHILIC SILICONE COMPOSITION

(71) Applicant: MOMENTIVE PERFORMANCE MATERIALS INC., Waterford, NY (US)

(72) Inventors: Shreedhar Bhat, Bangalore (IN); Sandeep Naik, Bangalore (IN); Anubhav Saxena, Bangalore (IN); Kenrick M. Lewis, Flushing, NY (US)

(73) Assignee: Momentive Performance Materials Inc., Waterford, NY (US)

( * ) Notice: Subject to any disclaimer, the term of this patent is extended or adjusted under 35 U.S.C. 154(b) by 91 days.

(21) Appl. No.: 14/102,025

(22) Filed: Dec. 10, 2013

(65) Prior Publication Data

US 2015/0158889 A1    Jun. 11, 2015

(51) Int. Cl.
| | |
|---|---|
| *C08F 30/08* | (2006.01) |
| *C07F 7/08* | (2006.01) |
| *C08F 220/18* | (2006.01) |
| *C08F 230/08* | (2006.01) |
| *C08G 77/20* | (2006.01) |
| *C08L 43/04* | (2006.01) |
| *C08L 83/04* | (2006.01) |
| *G02B 1/04* | (2006.01) |

(52) U.S. Cl.
CPC ............... *C07F 7/0854* (2013.01); *C07F 7/084* (2013.01); *C07F 7/0847* (2013.01); *C08F 220/18* (2013.01); *C08F 230/08* (2013.01); *C08G 77/20* (2013.01); *C08L 43/04* (2013.01); *C08L 83/04* (2013.01); *G02B 1/043* (2013.01)

(58) Field of Classification Search
CPC ........ G02B 1/043; C08G 77/20; C08F 220/18
See application file for complete search history.

(56) References Cited

U.S. PATENT DOCUMENTS

| | | |
|---|---|---|
| 3,408,429 A | 10/1968 | Wichterle |
| 3,496,254 A | 2/1970 | Wichterle et al. |
| 4,084,459 A | 4/1978 | Clark |
| 4,197,266 A | 4/1980 | Clark et al. |
| 4,260,725 A | 4/1981 | Keogh et al. |
| 5,352,714 A | 10/1994 | Lai et al. |
| 5,998,498 A | 12/1999 | Vanderlaan et al. |
| 6,013,711 A | 1/2000 | Lewis et al. |
| 6,207,782 B1 | 3/2001 | Czech et al. |
| 6,867,245 B2 | 3/2005 | Iwata et al. |
| 7,557,231 B2 | 7/2009 | Schorzman et al. |
| 7,601,766 B2 | 10/2009 | Schorzman et al. |
| 7,732,546 B2 | 6/2010 | Salamone et al. |
| 7,781,558 B2 | 8/2010 | Schorzman et al. |
| 7,825,273 B2 | 11/2010 | Schorzman et al. |
| 2007/0037944 A1 | 2/2007 | Almond et al. |

FOREIGN PATENT DOCUMENTS

| | | | |
|---|---|---|---|
| JP | 2004 085655 | * | 3/2004 |
| WO | 2013142062 | | 9/2013 |

OTHER PUBLICATIONS

JP 2004 085655 machine translation (2004).*
International Search Report and Written Opinion for International Application PCT/US2014/069084 dated Mar. 4, 2015.

* cited by examiner

*Primary Examiner* — Kuo-Liang Peng
(74) *Attorney, Agent, or Firm* — Joseph S. Ostroff, Esq.; McDonald Hopkins LLC

(57) ABSTRACT

A composition comprising a carbocyclic group and a hydrophilic moiety attached thereto an alpha, beta-unsaturated organosilicon compound. Such compounds are useful in developing water absorbing silicone-hydrogel films. Silicone-hydrogel films provide increased oxygen to pass through a lens or other treated materials.

32 Claims, No Drawings

HYDROPHILIC SILICONE COMPOSITION

FIELD

The present subject matter relates to a silicone monomer, macromer, polymers and hydrogels produced therefrom. The present subject matter provides, in one aspect, water dispersible hydrophilic silicone monomers and macromers capable of undergoing free-radical polymerization. The hydrophilicity of the described monomers, macromers, and pre-polymers comes from the ionic or non-ionic groups or both linked to the siloxane unit. The present subject matter also relates to hydrogel compositions and films suitable for producing biomedical products including contact lenses.

BACKGROUND

Contact lenses for continuous wear over a long term are made of silicone rubber prepared from polydimethyl siloxanes. Since the silicone rubber contact lenses are very water-repellent and greatly different from the cornea in thermal properties, such as thermal conductivity and thermal diffusivity, they give a foreign body sensation, particularly a burning sensation despite having oxygen permeability. Contact lenses made from silicone rubber are uncomfortable to wear. Further, the silicone rubber is soft and elastic, making it difficult to conduct precise mechanical treatments such as cutting, grinding, and polishing. Many attempts for making the surface of silicone rubber lenses hydrophilic have been undertaken, but no completely satisfactory contact lens has been developed. High water content contact lenses are usually made of poly-N-vinylpyrrolidone polymers. Since the high water content contact lenses contain about 60% to about 80% by weight of water, they have the disadvantages that they are (a) weaker in quality of material than low water content contact lenses, (b) easily contaminated with inorganic and organic compounds in tears which penetrate and accumulate into the lenses during the use, and (c) bad in maintenance of lens contour due to the evaporation of water during the use and, therefore, the refractive power thereof easily changes.

Reactive silicone-hydrogel formulations are used to make extended wear soft contact lenses due to their relatively high oxygen permeability, flexibility, comfort, and reduced corneal complications. Conventional hydrogel materials (e.g. 2-hydroxyethyl methacrylate, HEMA) by themselves have poor oxygen permeability and they transport oxygen to the eye through the absorbed water molecules. Water has low oxygen permeability, also called the Dk value, which may be expressed in Barrer, wherein 1 Barrer=$10^{-11}$ ($cm^3$ $O_2$) cm $cm^{-2}$ $s^{-1}$ $mmHg^{-1}$ where "$cm^3$ $O_2$" is at a quantity of oxygen at standard temperature and pressure and where "cm" represents the thickness of the material and "$cm^{-2}$" is the reciprocal of the surface area of that material. The Dk of water is 80 Barrer. Upon exposure to atmospheric air for long periods, these lenses are slowly dehydrated and the amount of oxygen transported to the cornea is reduced. Eye irritation, redness and other corneal complications can result and hence restrict use of the lenses to limited periods of wear. But blending reactive silicone monomers with conventional monomers as a potential solution have been marred by compatibility issues.

A possible solution to this problem is to make the silicone monomer inherently hydrophilic by incorporating hydrophilic units on the monomer. One approach to provide hydrophilic silicone monomers is to polymerize the organo-modified silicone monomer with organic monomers in the presence of a cross-linker. Examples of prior attempts of providing hydrophilicity include those described in U.S. Pat. Nos. 4,260,725; 5,352,714; 5,998,498; 6,867,245; 6,013,711; 6,207,782; 7,601,766; 7,557,231; 7,732,546; 7,781,558; 7,825,273, which are each incorporated herein by reference. This approach leads to a large number of unreacted monomers due to unregulated viscosity build-up that requires extracting the leachable monomers from the matrix by water-isopropanol solvent mixtures, which leads to increased processing costs. Further, the silicone hydrogel formulations made by these methods still fail to exhibit significant wettability.

Methacryloxypropyltris-(trimethylsiloxy)silane monomers have been used to prepare silicone-containing hydrogels. The (meth)acryloxypropyltris-(trimethylsiloxy)silane is hydrophobic and is used in preparing polyurethane-silicone polymers. These polyurethane-silicone polymers contain blocks of hydrophobic silicone. Contact lenses made from these polymers may cause eye discomfort because of the hydrophobic regions within the polymer.

Silicone-hydrogels are typically made from acrylate or methacrylate functionalized silicone monomer that are polymerized with hydrophilic organic monomers, such as hydroxyethyl methacrylate (HEMA), N-vinylpyrrolidone (NVP) and other monomers such as methyl methacrylic acid (MA), and N,N-dimethylacrylamide (DMA), in the presence of crosslinkers and free radical or photoinitiators. Crosslinking agents generally have two or more reactive functional groups at different sites of the molecule. Typically, these sites contain polymerizable ethylenic unsaturation groups. During polymerization to form the silicone-hydrogel, they form a covalent bond with two different polymer chains and form a stable three-dimensional network to improve the strength of the polymer. Crosslinking agents conventionally used in contact lenses include ethylene glycol dimethacrylate and trimethyloylpropane trimethacrylate. Other useful crosslinking agents include diethyleneglycol dimethacrylate, bisphenol A dimethacrylate, diglycidyl bisphenol A dimethacrylate, and dimethacrylate-terminated polyethylene glycol, and reactive linear polyether modified silicones. The oxygen permeability of these silicone-hydrogels is affected by the chemical structure of the acrylate or methacrylate functionalized silicone monomer and choice of the other monomers containing reactive carbon-carbon double bonds that are used in preparing the crosslinked polymer.

Silicone-hydrogel contact lens materials are typically made using either hydrophobic mono-functional silicone monomers or multi-functional hydrophilic silicone monomers followed by secondary surface treatment. Mono-functional silicone monomers are often used in the contact lens industry over multi-functional silicone monomers since the latter lead to increased rigidity in the lenses made therefrom. The known mono-functional silicone monomers, however, may have deficiencies. For example, monofunctional siloxane-polyether (meth)acrylates are susceptible to air oxidation. Monofunctional (meth)acryloxy functional siloxanes that contain 1,4-substition on the (meth)acryloxy group to the siloxane group on a six-member ring, such as for example, (meth)acrylic acid 2-hydroxy-4-[2-bis-(trimethylsiloxy)methylsilanyl-ethyl]-cyclohexyl ester, form highly ordered copolymers which may inhibit the permeability of oxygen through the silicone-hydrogel. 1,3-substitution of the (meth)acryloxy group to the siloxane group on a six-member ring, such as for example, (meth)acrylic acid 2-hydroxy-5-[2-bis-(trimethylsiloxy)methylsilanyl-ethyl]-cyclohexyl ester, form less order copolymers, but the moderate polarity of the (meth)acryloxy group may affect the hydrophilic properties of the silicone-hydrogel.

The state of this art for soft contact lenses, including the silicone-based materials described in the above mentioned patents, still possess major shortfalls like formulation compatibility, sub-optimal surface wettability, lipid deposition, the need for compatablizers in preparing the polymer, internal wetting agents, or post processing treatments such as "plasma oxidation" surface treatments. These approaches can decrease oxygen permeability or require the use of compatabilizers, which add costs during the manufacturing process. There remains a need for hydrophilic silicone monomers with advantageous wettability and oxygen permeability that can be used to make contact lenses without the drawbacks and expensive surface treatments necessary with the native silicone containing materials of the current state of art.

Hence, there remains a need for hydrophilic silicone monomers with inherently advantageous wettability, stability to air oxidation, high oxygen permeability and high solubility in the other reactive monomers used to make the polymer without the need for compatibilizers.

SUMMARY

The polymerizable, organosilicon compounds of the present subject matter, in which an alpha, beta-unsaturated ester or amido group and an ionic group is linked to the silicon atom through a hydroxycycloalkylene-containing group, can be used to make contact lenses with improved wettability, oxidative instability, oxygen permeability, and without the need for the expensive surface treatments, processing costs associated with using compatibilizers or the less hydrophilic silicone containing monomers of the present art.

In one aspect, the present invention provides a composition comprising an alpha, beta-unsaturated organosilicon compound having the structure of Formula (1):

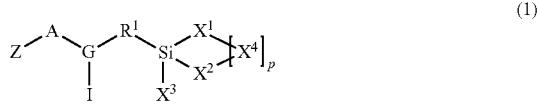

(1)

wherein:

$X^1$ is independently selected from linear or branched alkyl group containing 1-16 carbon atoms, trimethoxy silyl, trimethylsilyloxy, $-O[Si(CH_3)_2O-]_n$ wherein n is an integer chosen from 1 to 9, $(CH_3)_3Si(CH_2)_oCH_2-$ wherein o is an integer from 0-3, $(CH_3)_3SiCH_2CH_2Si(CH_3)_2O-$, or $(CH_3)_3Si(CH_2CH_2Si(CH_3)_2O)_p-$ wherein p is an integer chosen from 0-200;

$X^2$ is independently selected from linear or branched alkyl group containing 1-16 carbon atoms, trimethoxy silyl, trimethylsilyloxy, $-O[Si(CH_3)_2O-]_n$ wherein n is an integer chosen from 1 to 9, $(CH_3)_3Si(CH_2)_oCH_2-$ wherein o is an integer from 0-3, $(CH_3)_3SiCH_2CH_2Si(CH_3)_2O-$, or $(CH_3)_3Si(CH_2CH_2Si(CH_3)_2O)_p-$ wherein p is an integer chosen from 0-200, or $-[OSi(CH_3)_2]_mG^1$, wherein $G^1$ is $(CH_3)_3SiO-$, or a reactive or non reactive silicone group with the general Formula (2a) or (2b):

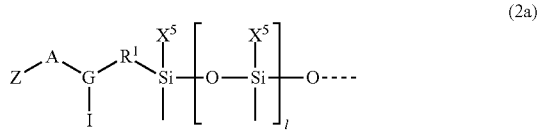

(2a)

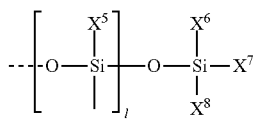

(2b)

where l is an integer chosen from 0-200; and p in Formula 1 is 0 when $X^2$ is of the Formula (2a) or 2(b);

$X^3$ and $X^5$ are independently chosen from methyl, butyl, trimethylsiloxy, $(CH_3)_3SiCH_2CH_2-$, $(CH_3)_3SiCH_2CH_2Si(CH_3)_2O-$ or $-OSi(CH_3)_2$, with the provisos that (i) when $X^1$ or $X^6$ is $-O[Si(CH_3)_2O-]_n$, then one of $X^3$ or $X^5$ is $-OSi(CH_3)_2$ and $X^1$ forms a chemical bond with the $X^3$ and/or $X^5$ forms a chemical bond with $X^6$ to correspondingly form a divalent $-X^1-X^3-$ or $X^5-X^6-$ group, which is bonded to the silicon atom to form a cyclic polysiloxane ring, and (ii) when $X^3$ and/or $X^5$ is $-OSi(CH_3)_2$, then $X^1$ and/or $X^6$ is $-O[Si(CH_3)_2O-]_n$ and the corresponding $X^1$ forms a chemical bond with the $X^3$ and/or $X^5$ forms a chemical bond with $X^6$ to form a divalent $-X^1-X^3-$ or $X^5-X^6-$ group, which is bonded to the silicon atom to form a cyclic polysiloxane ring; or $X^1$, $X^2$, and $X^3$ optionally are each $-O[Si(R^{16})O-]_n$ and interconncected to form a polysilsequioxane ring as described in formula (2c)

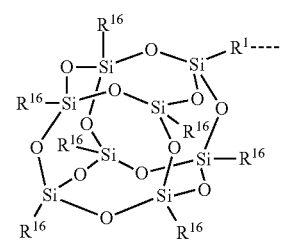

(2c)

wherein $R^{16}$ is independently chosen from a linear or branched alkyl or aralkyl group;

$X^4$ is an optional connecting group selected independently from dimethylsiloxy, $-O[Si(CH_3)_2O-]$, or $-CH_2CH_2(CH_3)_2SiO$-moiety, p is an integer chosen from 0-5;

$X^6$, $X^7$, and $X^8$ are independently chosen from a linear or branched alkyl group containing 1-16 carbon atoms, alkoxy, trimethylsilyloxy, or $-O[Si(CH_3)_2O-]_n$, wherein n is an integer chosen from 1 to 9, and wherein $X^6$ and $X^7$, $X^7$ and $X^8$, or $X^6$ and $X^8$ may form a ring;

$R^1$ is chosen from a chemical bond or an alkylene group containing from 1 to 16 carbon atoms and optionally containing a heteroatom of oxygen, sulfur and/or nitrogen;

G is a bridging unit between the siloxane moiety and reactive moiety independently selected from a linear or branched alkyl group or a carbocyclic group, the G unit optionally containing one or more heteroatoms;

A is a heteroatom;

I is a hydrophilic moiety with 0-100 carbon atoms which may contain heteroatoms;

Z is a polymerizable group of Formula (3):

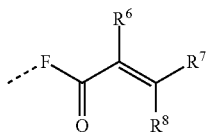
(3)

wherein $R^6$, $R^7$, and $R^8$ are independently selected from hydrogen or monovalent hydrocarbon radical with 1-5 carbon atoms; and F is an optional linker group chosen from aliphatic, cycloaliphatic, or aromatic hydrocarbon radical of 1 to about 16 carbons and optionally contains heteroatoms, with the proviso that if F is not utilized, then A is directly linked to the carbonyl group in Formula (3).

In one aspect, the composition is a copolymer comprising the organosilicon compound.

In one aspect, the composition is a hydrogel. In still another aspect, the present invention provides an article formed from the hydrogel comprising the organosilcon compound. In one embodiment, the article is a contact lens.

DETAILED DESCRIPTION

The present subject matter provides compositions comprising alpha, beta-unsaturated organosilicon compounds having the structure of Formula (1):

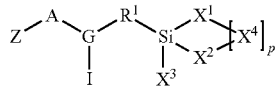
(1)

wherein:

$X^1$ is independently selected from linear or branched alkyl group containing 1-16 carbon atoms, trimethoxy silyl, trimethylsilyloxy, $-O[Si(CH_3)_2O-]_n$ wherein n is an integer chosen from 1 to 9, $(CH_3)_3Si(CH_2)_oCH_2-$ wherein o is an integer from 0-3, $(CH_3)_3SiCH_2CH_2Si(CH_3)_2O-$, or $(CH_3)_3Si(CH_2CH_2Si(CH_3)_2O)_p-$ wherein p is an integer chosen from 0-200.

$X^2$ is independently selected from linear or branched alkyl group containing 1-16 carbon atoms, trimethoxy silyl, trimethylsilyloxy, $-O[Si(CH_3)_2O-]_n$ wherein n is an integer chosen from 1 to 9, $(CH_3)_3Si(CH_2)_oCH_2-$ wherein o is an integer from 0-3, $(CH_3)_3SiCH_2CH_2Si(CH_3)_2O-$, or $(CH_3)_3Si(CH_2CH_2Si(CH_3)_2O)_p-$ wherein p is an integer chosen from 0-200, or $-[OSi(CH_3)_2]_mG^1$, wherein $G^1$ is $(CH_3)_3SiO-$, or a reactive or non reactive silicone group with the general Formula (2a) or (2b):

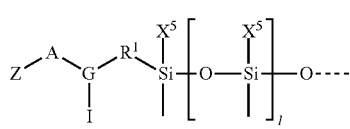
(2a)

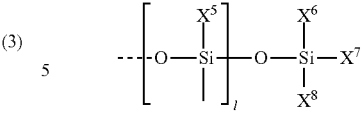
(2b)

where l is an integer chosen from 0-200; and p in Formula 1 is 0 when $X^2$ is of the Formula (2a) or 2(b);

$X^3$ and $X^5$ are independently chosen from methyl, butyl, trimethylsiloxy, $(CH_3)_3SiCH_2CH_2-$, $(CH_3)_3SiCH_2CH_2Si(CH_3)_2O-$, and $-OSi(CH_3)_2$, with the provisos that (i) when $X^1$ or $X^6$ is $-O[Si(CH_3)_2O-]_n$, then $X^3$ and $X^5$, respectively, is $-OSi(CH_3)_2$ and $X^1$ forms a chemical bond with the $X^3$ and $X^5$ forms a chemical bond with $X^6$ to correspondingly form a divalent $-X^1-X^3-$ or $X^5-X^6-$ group, which is bonded to the silicon atom to form a cyclic polysiloxane ring, and (ii) when $X^3$ and/or $X^5$ is $-OSi(CH_3)_2$, then $X^1$ and/or $X^6$ is $-O[Si(CH_3)_2O-]_n$, and $X^1$ forms a chemical bond with the $X^3$ and/or $X^5$ forms a chemical bond with $X^6$ to form a divalent $-X^1-X^3-$ or $X^5-X^6-$ group, which is bonded to the silicon atom to form a cyclic polysiloxane ring;

where, $X^1$, $X^2$ and $X^3$ optionally can each be $-O[Si(R^{16})O-]_n$, and interconncected to form a polysilsequioxane ring as described in formula (2c) and $R^{16}$ is independently chosen from a linear or branched alkyl or aralkyl group;

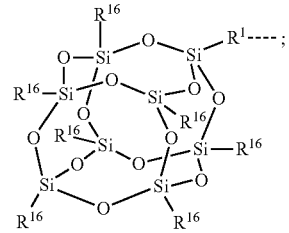
(2c)

$X^6$, $X^7$, and $X^8$ are independently chosen from a linear or branched alkyl group containing 1-16 carbon atoms, alkoxy, trimethylsilyloxy, or $-O[Si(CH_3)_2O-]_n$, wherein n is an integer chosen from 1 to 9, and wherein $X^6$ and $X^7$, $X^7$ and $X^8$, or $X^6$ and $X^8$ may form a ring;

$X^4$ is an optional connecting group selected independently from dimethylsiloxy, $-O[Si(CH_3)_2O-]$, or $-CH_2CH_2(CH_3)_2SiO$-moiety;

p is an integer chosen from 0-5;

$R^1$ is generally a chemical bond or an alkylene group containing from 1 to 16 carbon atoms and optionally a heteroatom of oxygen, sulfur or nitrogen;

G is a bridging unit between the siloxane moiety and reactive moiety independently selected from a linear or branched alkyl group or a carbocyclic group optionally contains hetero atoms;

A is a heteroatom, and in one embodiment is chosen between oxygen or sulfur;

I is a hydrophilic moiety with 0-100 carbon atoms which may contain heteroatoms;

Z is a polymerizable group having the general Formula (3):

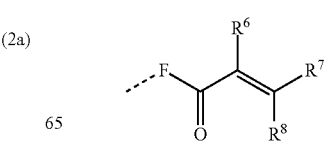
(3)

wherein:

$R^6$, $R^7$, and $R^8$ are independently chosen from hydrogen or monovalent hydrocarbon radical with 1-5 carbon atoms; and F is a linker group chosen from aliphatic, cycloaliphatic or aromatic hydrocarbon radicals of 1 to about 16 carbons optionally contains heteroatoms. G is a substituted carbocyclic unit having an I group attached hereto.

In one embodiment, the unit G links the A unit and the $R^1$ unit. In one embodiment, G is a branched alkyl moiety with the general formula

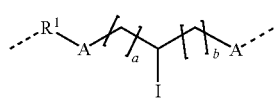

(4a)

wherein a is 0-16 and b is 1

In one embodiment, G comprises a saturated carbocyclic unit comprising 5 to 10 carbon atoms with the general formula (4b) wherein c=0-5.

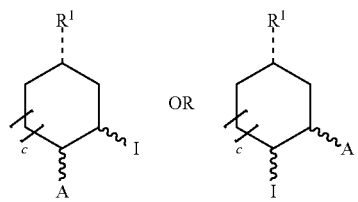

(4b)

In one embodiment, G is a cyclohexylene group. The A and R groups can be attached to the G group such that the A and R groups are oriented para or meta to one another. In one embodiment, the G unit is a cyclohexylene group and arranged in the compound as follows:

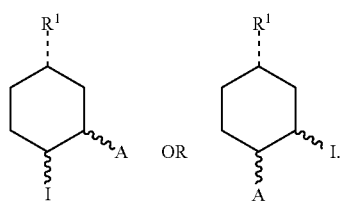

In one embodiment, G is a cyclohexylene chosen from one or a combination of the following positional isomers:

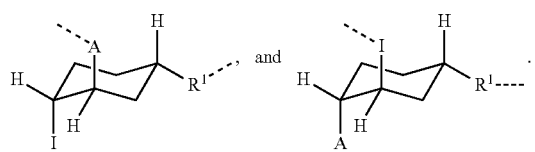

In one embodiment G is a chosen from one or more of the following conformers:

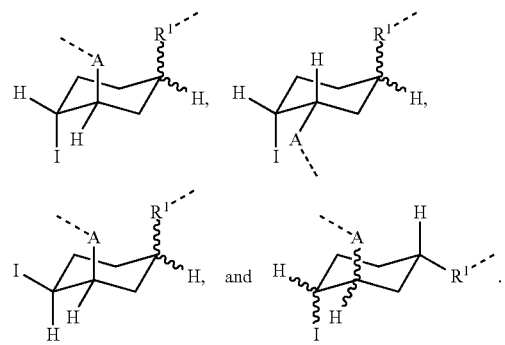

$R^1$ can be a chemical bond or an alkylene group comprising 1 to 16 carbon atoms and optionally a heteroatom chosen from oxygen, sulfur, or nitrogen. In one embodiment, $R^1$ is a divalent radical with the general structure:

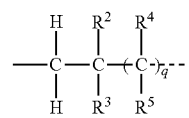

(5)

wherein $R^3$, $R^4$, and $R^5$ are independently chosen from hydrogen, a linear, branched, or cyclic hydrocarbon radical with 1 to 10 carbon atoms, optionally containing heteroatoms, $R^2$ is a hydrocarbon radical with 1 to 5 carbon atoms; and q is an integer chosen from 0 to 10.

Representative and non-limiting examples of $R^1$, $R^2$, $R^3$, $R^4$, and/or $R^5$ include hydrogen (for $R^3$, $R^4$, and/or $R^5$) methyl, ethyl, 2-methylethyl, propyl, 2-methylpropyl, carboxy, carboxymethyl, carboxyethyl, methoxycarbonylmethyl, ethoxycarbonylethyl, or a combination of two or more thereof.

I is a hydrophilic moiety with 0-100 carbon atoms and may contain heteroatoms. In one embodiment, I is a hydrophilic moiety of the general formula:

—K-L-M        (6)

wherein K is a divalent hetero atom, and in one embodiment is an oxygen atom,

L is an optional divalent hydrocarbon radical comprising a substituted or unsubstituted, linear or branched, aliphatic or aromatic hydrocarbon with 0-50 carbon atom, which may optionally contain heteroatoms, and in embodiments can comprise functionalities independently chosen from an alcohol, an ether, an ester, an amide, an amine, a urea, a urethane, a cyano, a carbonate, a carbamate, a thiol, a thioether, a thiol ester, or a combination of two or more thereof, and M is an ionic group independently chosen from —COOR, —NR$_2$, —PO(OR)$_2$, —OPO(OR)$_2$, —OSO$_3$H, —OH, wherein R is selected from hydrogen or hydrocarbon radicals with 1 to 10 carbon atoms. When L is a group that does not contain any carbon atoms then the M group cannot contain —NR$_2$, —OPO(OR)$_2$, —OSO$_3$H, or —OH groups.

In one embodiment, I is independently selected from the following structures:

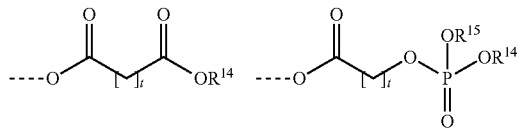

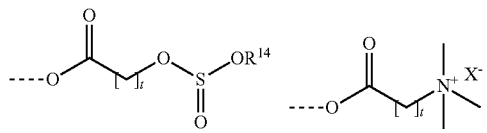

wherein $R^{14}$ and $R^{15}$ are independently selected from hydrogen, alkyl, aralkyl, or aromatic linear or branched units with 1-20 carbon atoms, or alkali or alkaline earth metal anions or transition metal complexes; $X^-$ is independently selected from a halide, a carboxylate, a tosylate, a sulfonate, a phosphate, a phthalate, a phenolate, an alkoxide etc., and t is an integer chosen from 1-16;

F is a linker group chosen from aliphatic, cycloaliphatic, or aromatic hydrocarbon radical having 1-16 carbon atoms and optionally containing a heteroatom. Optionally F is a bond such that the A group is directly linked to the carbonyl group in Formula (3). In one embodiment, F has the general formula:

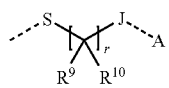 (7)

wherein r is an integer selected from 0 to about 15; S is a divalent heteroatom independently selected from O, $CH_2$, $NR^{11}$, or sulfur; J is independently selected from functional groups —C(O)—, —$NR^{12}$C(O)—, —OC(O)—, —OS(O)—, or —P(O)$OR^{13}$; $R^9$ and $R^{10}$ are independently chosen from a hydrocarbon radical with 1 to 5 carbon atoms; $R^{11}$, $R^{12}$ and $R^{13}$ are independently selected from hydrogen or a monovalent hydrocarbon radical with 1-5 carbon atoms. In one embodiment F has the following general structure:

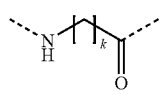 (8)

wherein k is 0-5.

In one embodiment a silicone monomer has the formula:

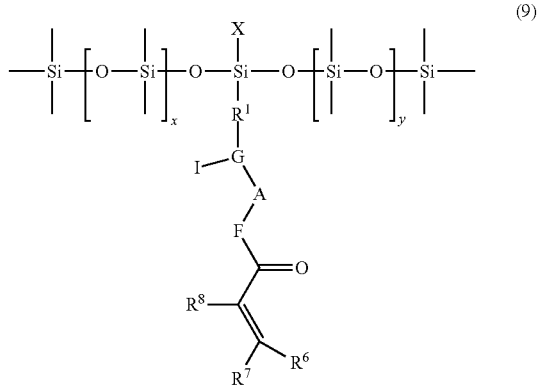 (9)

wherein x and y are integers chosen from 0-100, and $R^1$, $R^6$, $R^7$, $R^8$, A, F, G, I can be as described herein. X is independently chosen from linear or branched alkyl group containing 1-16 carbon atoms, alkoxy, trimethoxysilyl, trimethylsilyloxy, $(CH3)3Si[OSi(CH3)2]_qO$— wherein q is an integer chosen from 0-100. In one embodiment, $R^1$, $R^6$, $R^7$, $R^8$ are independently selected from linear or branched alkyl or aralkyl including, but not limited to, methyl, ethyl, propyl, butyl, etc.

In one embodiment, a silicone monomer has the formula:

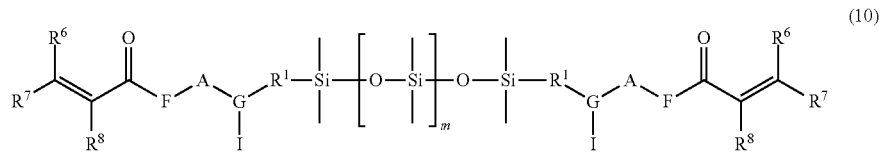 (10)

wherein m is an integer chosen from 0-200, and $R^1$, $R^6$, $R^7$, $R^8$, A, F, G, and I are as described herein. In one embodiment, $R^1$, $R^6$, $R^7$, $R^8$ are independently selected from linear or branched alkyl or aralkyl including but not limited to, methyl, ethyl, propyl, butyl, etc.

In one embodiment, a monomer structure is exemplified by the following formula:

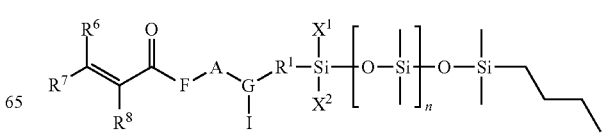 (11)

wherein n is an integer chosen from 0-200, and $R^1$, $R^6$, $R^7$, $R^8$, F, A, G, and I are as described herein. In one embodiment, $R^1$, $R^6$, $R^7$, $R^8$ are independently selected from linear or branched alkyl or aralkyl including but not limited to, methyl, ethyl, propyl, butyl, etc.

In yet another embodiment, a monomer structure is exemplified by the following formula:

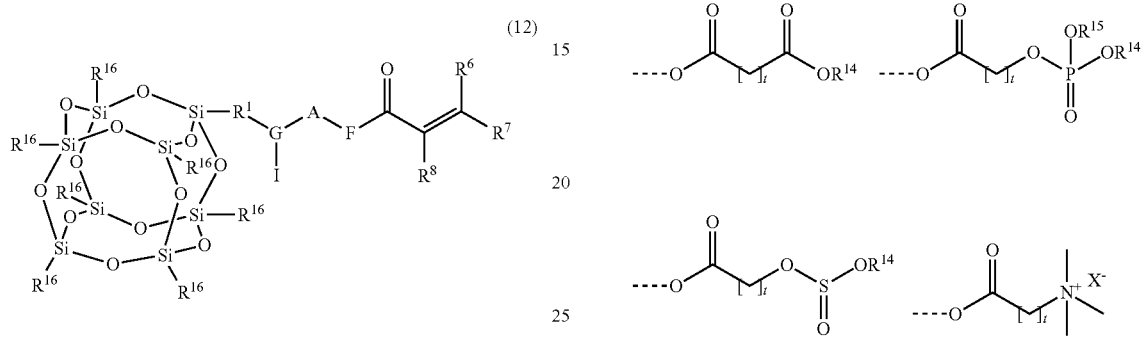

(12)

$R^1$, $R^6$, $R^7$, $R^8$, F, A, G, and I are as described herein. In one embodiment, $R^1$, $R^6$, $R^7$, $R^8$ are independently selected from linear or branched alkyl or aralkyl including but not limited to, methyl, ethyl, propyl, butyl, etc. $R^{16}$ is a monovalent hydrocarbon radical, linear or branched, optionally containing heteroatoms and hydroxyl groups having 1 to 40 carbon atoms. G has the following structures:

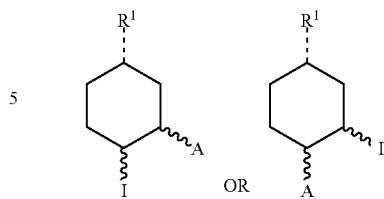

OR

I is independently selected from:

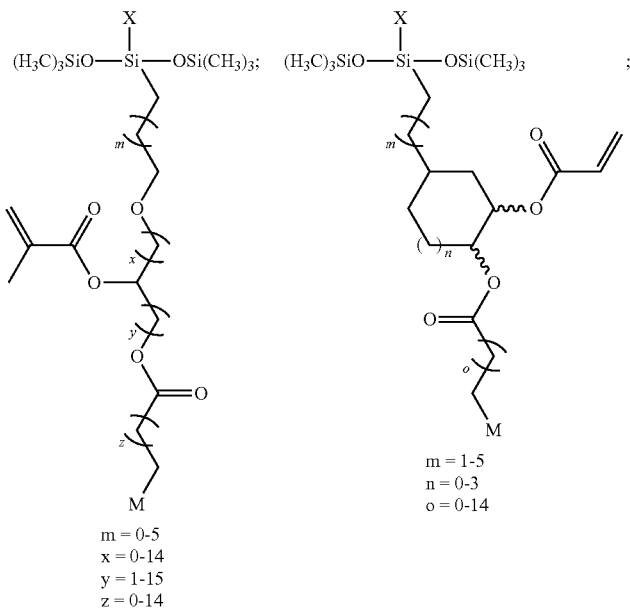

wherein $R^{14}$ and $R^{15}$ are independently selected from hydrogen, alkyl, aralkyl or aromatic linear or branched units with 1-20 carbon atoms, or alkali or alkaline earth metal anions or transition metal complexes; $X^-$ is independently selected from a halide, a carboxylate, a tosylate, a sulfonate, a phosphate, a phthalate, a phenolate, an alkoxide, etc., t is an integer chosen from 1-16. In one embodiment, F is a bond and A is directly linked to the carbonyl group.

Examples of suitable alpha, beta-unsaturated organosilicon compounds include, but are not limited to, $(H_3C)_3SiO\text{—}\underset{\underset{\text{OSi}(CH_3)_3}{|}}{\overset{\overset{X}{|}}{Si}}\text{—}$ ; $(H_3C)_3SiO\text{—}\underset{\underset{\text{OSi}(CH_3)_3}{|}}{\overset{\overset{X}{|}}{Si}}\text{—}$ ;

m = 0-5
x = 0-14
y = 1-15
z = 0-14 m = 1-5
n = 0-3
o = 0-14

-continued
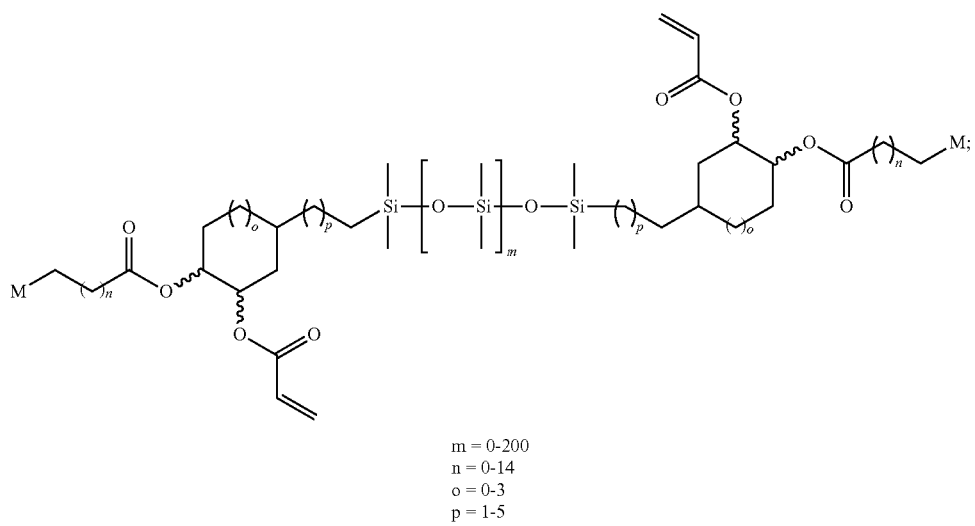
m = 0-200
n = 0-14
o = 0-3
p = 1-5
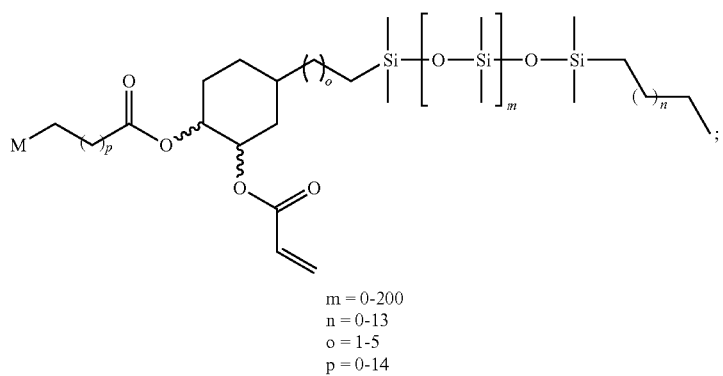
m = 0-200
n = 0-13
o = 1-5
p = 0-14
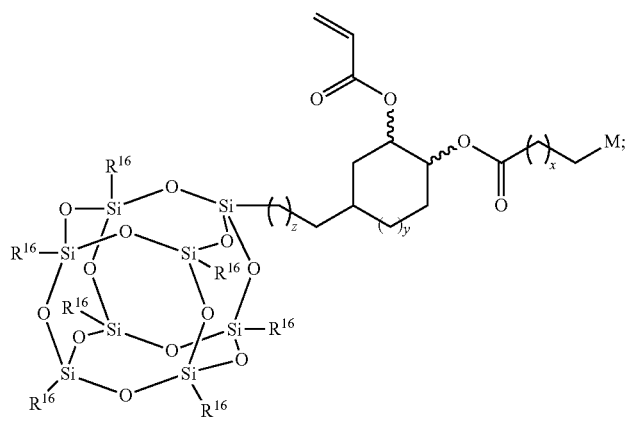
x = 1-5
y = 0-3
z = 0-14

-continued

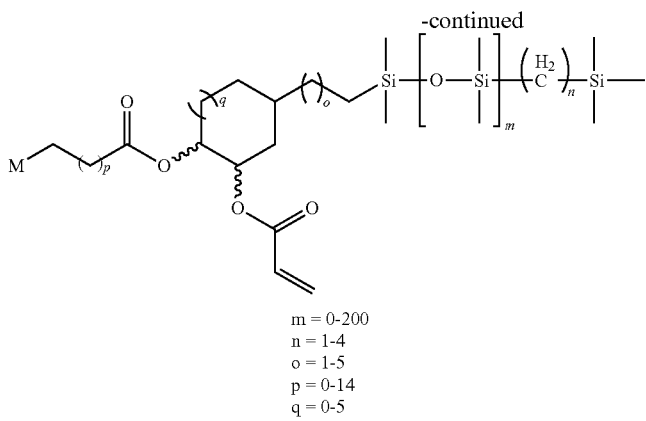

m = 0-200
n = 1-4
o = 1-5
p = 0-14
q = 0-5 wherein M is an ionic group independently chosen from —COOR, —NR$_2$, —PO(OR)$_2$, —OPO(OR)$_2$, —OSO$_3$H, and —OH and R is selected from hydrogen or hydrocarbon radicals with 1 to 10 carbon atoms; R$^{16}$ is a linear or branched, monovalent hydrocarbon radical, optionally containing one or more heteroatoms; X is independently chosen from a linear or branched alkyl group containing 1-16 carbon atoms, an alkoxy, a trimethoxysilyl, a trimethylsilyloxy, or (CH$_3$)$_3$Si [OSi(CH$_3$)$_2$]$_q$O— wherein q is an integer chosen from 0-100.

The present subject matter also provides hydrogel compositions comprising alpha, beta-unsaturated organosilicon compounds of the present subject matter may form a hydrogel. In one embodiment, the hydrogel may further include a free-radical polymerizable organic monomer, an initiator, and optionally a crosslinker. In one embodiment, the hydrogel composition may further comprise a hydrophilic silicone macromer that is present in an amount of from about 5 weight percent to about 50 weight percent of the hydrogel composition. In another embodiment, the ratio of a hydrophilic silicone macromer to a free-radical polymerizable organic monomer is from about 1:100 to about 100:about 1:50 to about 50:1, about 1:10 to about 10:1, or about 1:1.

Silicone hydrogel films obtained from alpha, beta-unsaturated organosilicon compounds of Formula (1) show high oxygen permeability due to the substitution of the alpha, beta-unsaturated carbonyloxy or alpha, beta-unsaturated carbonylthiolate on a cyclohexyl linking group, relative to the silicon-containing group. Although not to be held to any theory, the trans-1,3-substitution of the cyclohexyl group is believed to introduce more randomness (entropy) into the polymer containing the monomer of the present subject matter, thereby introducing a large free volume and better oxygen permeability. The ionic functional groups of the compounds of the present subject matter, along with the hydrophilic monomers allow the silicone hydrogel films to have sufficient amounts of water and small enough regions of silicone containing units to provide for films that do not cause eye irritation, redness and other corneal complications which may result from direct contact of the eye with regions of high silicone content and hence restrict use of the lenses to limited periods of wear.

The alpha, beta-unsaturated organosilicon compounds of the present subject matter having Formula (1) can be used to obtain cured elastomers with desirable physical strength and resistance to tearing after absorption of water. The use of alpha, beta-unsaturated organosilicon compounds of Formula (1) in biomedical devices, especially in contact lenses, is further described in the sections below.

The present subject matter also provides silicone-hydrogel compositions comprising alpha, beta-unsaturated organosilicon compounds of Formula (1) and at least one conventional organic monomer (also called co-monomer). The novel copolymers comprise one or more of the alpha, beta-unsaturated organosilicon compounds of Formula (1) copolymerized with one or more of an alkyl 2-alkenoate, cycloalkyl 2-alkenoate, vinyl-containing aryl compound, vinyl-containing aralkyl compound and a relatively small amount of a cross-linking monomer. In general, novel copolymers containing from 20 to 80 parts by weight of the alpha, beta-unsaturated organosilicon compounds of Formula (1) and from 80 to 20 parts of the 2-alkenoate, vinyl-containing aryl, vinyl-containing aralkyl monomer having a wide spectrum of suitable properties can be prepared. In one embodiment of the subject matter, the novel copolymers contain 30 to 55 parts by weight of alpha, beta-unsaturated organosilicon compounds of Formula (1) copolymerized with 70 to 45 parts by weight of a C$_1$-C$_4$ alkyl methacrylate and/or acrylate, and/or a cyclohexyl methacrylate and/or acrylate, preferably with a small amount of a cross-linking monomer.

Representative and non-limiting co-monomers include methyl methacrylate, ethyl methacrylate, butyl methacrylate, 2-ethylhexyl acrylate, cyclohexyl methacrylate, methyl acrylate, 2-hydroxyethyl methacrylate (HEMA), N-vinylpyrrolidone (NVP), methacrylic acid (MA), and dimethylacrylamide (DMA), styrene (vinyl benzene), alpha-methylstyrene, N-vinyl-caprolactam, N-vinyl-acetamide, N-vinyl-formamide, N-vinyl-isopropylamide, vinyl naphthalene, vinyl pyridine, vinyl alcohol, vinyl containing silicones, 3-[tris(trimethylsiloxy)silyl]propyl methacrylate; methyl-di (trimethylsiloxy)-silyl propyl glycerol methacrylate; 3-(trimethylsilyl)propyl vinyl carbonate; 3-(vinyloxycarbonylthio)propyl-[tris(trimethylsiloxy)silane]; 3-[tris(tri-methylsiloxy)silyl]propyl vinyl carbamate; 3-[tris(trimethylsiloxy)silyl]propyl allyl carbamate; 3-[tris(trimethylsiloxy) silyl]propyl vinyl carbonate and mixtures thereof.

The cross-linking agent may be present in an amount of up to 5 weight percent and higher, desirably from 0.1 to 3 weight percent, and preferably up to 2 weight percent, based on the total monomers. The cross-linking agent, including mixtures thereof, can be any of the conventional ethylenically unsaturated compounds containing at least two polymerizable ethylenic bonds. Thus, there can be used alkylene glycol and polyalkylene glycol esters of acrylic acid, methacrylic acid, or crotonic acid and divinylbenzene. Representative and non-limiting examples of crosslinkers include ethylene glycol diacrylate, ethylene glycol dimethacrylate, propylene glycol diacrylate, propylene glycol dimethacrylate, 1,4-butylene glycol dimethacrylate, ethylene glycol dicrotonate, diethylene glycol dimethacrylate, diethylene glycol diacrylate, dipropylene glycol dimethacrylate, dipropylene glycol diacrylate, trimethylene glycol diacrylate, triethylene glycol dimethacrylate, triethylene glycol dicrotonate, tetraethylene glycol dimethacrylate, hexaethylene glycol dimethacrylate, tripropylene glycol diacrylate, tripropylene glycol dimethacrylate, tetrapropylene glycol dimethacrylate, tributylene glycol dimethacrylate, tetrabutylene glycol dimethacrylate, hexamethylene glycol dimethacrylate, octamethylene glycol dimethacrylate, and decamethylene glycol dimethacrylate. Other suitable cross-linking agents include allyl methacrylate, divinylbenzene, diallyl phthalate, trimethylolpropane trimethacrylate, diallyl tartrate, diallyl maleate, triallylmelamine, N,N'-methylenebisacrylamide, divinyl citraconate, diallyl fumarate, divinyl sulfone, triallyl phosphite, diallyl benzenephosphonate, hexahydro-1,3,5-triacryltriazine, divinyl ether, and triallyl citrate. Also useful as cross-linking agents are the polysiloxanyl-containing polyethylenically unsaturated compounds such as polysiloxanylbis(alkylglycerol acrylate) and polysiloxanylbis (alkylglycerol methacrylate).

The alpha, beta-unsaturated organosilicon compounds of the present subject matter having Formula (1) are desirably miscible with hydrophilic co-monomers without the need for any homogenizing solvents, thereby affording silicone hydrogels that are transparent across the entire range of monomer-co-monomer compositions.

The high oxygen permeability of the novel copolymers is also due to its siloxane content. The oxygen permeability of the hydrogel films can be extended up to 170 Dk units when silicone monomers described in the current subject matter is used along with siloxane and polysiloxane analogues known in the art. However, the greater the number of siloxane bonds in the novel copolymer, the greater the tendency of an undesirable water-repellent characteristic developing in the polymer. In such an eventuality it may be desirable to include in the polymerization mixture hydrophilic monomer such as the 2-hydroethyl methacrylate, 2-hydroethyl acrylate, N-vinylpyrrolidone, N,N-dimethylacrylamide along with other co-monomers.

In another embodiment of the present subject matter, the polymers can be formed into silicone-hydrogel films, via processes known in the art. The silicone-hydrogel films of the present subject matter are soft, flexible and highly transparent. Silicone-hydrogel films made from the inventive monomers exhibit better surface wettability and sufficiently oxygen permeable compared to ones made using monomers having linear alkyl linked methacrylated silicone polyether chains. The present silicone hydrogel films are found to have dynamic advancing contact angles with water, in the range of 100° to 25°, receding contact angle in the range of 60° to 15° which can vary depending on the molecular weight of the polyethers or siloxanes. The contact angle can also be altered in the defined range by adding wetting agents like poly(vinyl pyrrolidone), poly(vinyl alcohol), and hydroxyalkyl cellulose etc.

Polymerization can be carried out under conventional conditions. Thus, for example, polymerization can be carried out specifically at 20° C. to 80° C. and more specifically at 25° to 45° C. The polymerization can be carried out employing a catalytically significant quantity of a free radical catalyst ranging in concentration from 0.05 to 1 percent based on the total weight of polymerizable monomers. Representative and non-limiting free radical catalysts include t-butyl peroctoate, benzoyl peroxide, isopropyl percarbonate, 2,4-dichlorobenzoyl peroxide, methyl ethyl ketone peroxide, cumene hydroperoxide, and dicumyl peroxide. Additional free radical polymerization initiators that can be used include, but are not limited to, bis-(tert-butylcyclohexyl)-peroxydicarbonate, azobisisobutyronitrile, and azobisdimethylvaleronitrile. Irradiation by ultraviolet light, gamma rays, and high-energy radiation, such as with cobalt 60 radiation can be used to polymerize the monomers.

The copolymers of the present subject matter are clear (no haze from poor miscibility) polymers that absorb 10 weight percent to 60 weight percent of water, showing excellent surface wettability and effective oxygen permeability, all of which are necessary for the better comfort when lens are worn and for good health of the human cornea. The present subject matter also provides contact lenses made from the silicone-hydrogel films of the claimed subject matter. The contact lenses produced from the silicone-hydrogel films of the present subject matter do not require any expensive secondary treatments, like plasma oxidation or plasma coating, or internal wetting agents to improve wettability. That is, the contact lenses produced from silicone-hydrogel films of the present subject matter, without secondary treatment, are soft, flexible, and inherently wettable and exhibit high oxygen permeability.

The present subject matter is also directed to copolymers formed by the reaction alpha, beta-unsaturated organosilicon compounds of Formula (1) with other activated carbon-carbon double bond containing monomers and crosslinkers. These copolymers are made from one or more alpha, beta-unsaturated organosilicon compounds of Formula (1) and at least one other hydrophilic unsaturated organic monomer suitable for use in silicone hydrogels. These hydrophilic unsaturated organic monomers include the representative and non-limiting examples N,N-dimethylacrylamide, 2-hydroxyethyl-methacrylate (HEMA), N-vinylpyrrolidone, and methacrylic acid. In such copolymers, the copolymer ratio of the alpha, beta-unsaturated organosilicon compounds of Formula (1) to the other activated carbon-carbon double bond containing monomers is from 1:100 to 100:1, preferably from 1:20 to 20:1 and more preferably from 1:2 to 2:1.

In one particular embodiment, a copolymer is prepared from 40 to 60 weight percent of alpha, beta-unsaturated organosilicon compounds of Formula (1), 20 to 30 weight percent of dimethylacrylamide, 15 to 25 weight percent 2-hydroxyethyl(meth)acrylate, 1 to 10 weight percent N-vinyl pyroline and 0.1 to 3 weight percent of ethylene glycol dimethyl acrylate, based on the total weight of alpha, beta-unsaturated organosilicon compounds of Formula (1), dimethylacrylamide, 2-hydroxyethyl(meth)acrylate, N-vinyl pyrrolidone and ethylene glycol dimethyl acrylate.

To form copolymers using the monomers of the present subject matter, the desired monomers are mixed and the resulting mixture is polymerized and cured to form transparent thin films by known thermal or UV cure techniques, using either peroxides or photoinitiators in the presence of crosslinking agents. The hydrogels films are cured within 20-60 seconds of UV irradiation when hydroxymethyl propiophenone and biacyl phosphine oxide are used as photoinitiators and the UV radiation has a wavelength of 365 nm. The monomers added to the monomer mix to create the mixture named as formulation or formula prior to polymerization to form the copolymers may be monomers or prepolymers. A "prepolymer" is a reaction intermediate polymer of medium molecular weight having polymerizable groups.

The copolymers of the present subject matter form a clear, transparent homogeneous single-phase solution that can be cured directly without employing any additional homogenizing solvents. The alpha, beta-unsaturated organosilicon compounds of Formula (1) are miscible with hydrophilic hydrogel monomers. Calculated solubility parameter values based on Fedors method (Robert F. Fedors, Polymer Engineering and Science, February 1974, vol. 14, No. 2) for the present inventive monomers range from approximately 16.5 to approximately 19 $(J/mol)^{1/2}$, which is closer to the solubility parameter value of conventional hydrogel monomers (such as HEMA, NVP and DMA) than silicone monomers such as TRIS. Miscibility is realized if the difference in solubility parameter between the instant inventive monomers and the hydrophilic co-monomers is less than about 7.3 $(J/mol)^{1/2}$.

In another embodiment of the present subject matter, the polymers may be formed into silicone-hydrogel films, by processes known in the art. The silicone-hydrogel films of the present subject matter are soft, flexible and highly transparent. The present silicone hydrogel films are found to have dynamic advancing contact angles with water, in the range of 80° to 30° and absorb about 10 to 60 wt. % of water, which can vary depending the other hydrophilic unsaturated organic monomer used in preparing the silicone-hydrogel films. The silicone hydrogels produced are also found to have good mechanical properties (such as low modulus and high tear strength) required for the contact lens application.

Conventional silicone-hydrogel films are generally produced by curing a mixture of hydrophobic silicone monomers and hydrophilic hydrogel monomers in the presence of about 10 to 40 wt. % of solvent, as they are incompatible with each other. However, in the current subject matter, the alpha, beta-unsaturated organosilicon compounds of Formula (1) are generally miscible with conventional hydrophilic hydrogel monomers (such as HEMA, NVP and DMA) and can form a homogeneous solution suitable to produce silicone-hydrogel films without employing any solvent. More specifically, near 100% siloxane monomer alone of the subject matter can be used to make stable hydrogel films using appropriate molds, which is not possible with the linear alkyl linked trisiloxane polyether methacrylates In the present subject matter, the resulting polymer compositions may be formed into silicone-hydrogel films, via processes known in the art. Accordingly, the present subject matter is also directed to contact lens produced from either homo or copolymers of the present subject matter. The monomers/polymers of the present subject matter can be formed into contact lenses by spincasting processes, as disclosed in U.S. Pat. Nos. 3,408,429 and 3,496,254, cast molding processes, as disclosed in U.S. Pat. Nos. 4,084,459 and 4,197,266, combinations of methods thereof, or any other known method for making contact lenses.

Polymerization may be conducted either in a spinning mold, or a stationary mold corresponding to a desired contact lens shape. The lens may be further subjected to mechanical finishing, as occasion demands. Polymerization may also be conducted in an appropriate mold or vessel to form buttons, plates or rods, which may then be processed (e.g., cut or polished via lathe or laser) to give a contact lens having a desired shape.

The relative softness or hardness of the contact lenses fabricated from the resulting polymer of this subject matter can be varied. Generally, as the ratio of alpha, beta-unsaturated organosilicon compounds of Formula (1) increases relative to the other monomers used in preparing the polymer, the softness of the material increases.

The copolymers of this subject matter may also contain ultraviolet absorbents, pigments and colorants in the form of additives or co-monomers.

The silicone-hydrogels of the present subject matter exhibit high oxygen transport with surface wettable properties. The monomers and prepolymers employed in accordance with this subject matter are readily polymerized to form three-dimensional networks, which permit the transport of oxygen with improved wettability along with desirable mechanicals and optical clarity. The oxygen permeability of hydrogel films of instant invention can be further extended up to 300 Dk units when combinations of different siloxane systems are formulated.

Specific use of the films include intraocular contact lenses, artificial corneas, and soft disposable long-wear contact lenses or as coatings for biomedical devices, or any part thereof. Additional uses may include a film forming additive in a textile, paper, leather, personal care, health care, home care, coating, painting or seed treatment formulations.

In one aspect the present subject matter, the polymer can be homopolymer or copolymers. The homopolymers and copolymers can be prepared as an emulsion, waterborne dispersion, solution, latex particles or 100% active compositions. Emulsions can be prepared through free radical polymerization in the presence of water and emulsifiers. These homopolymers, copolymers, waterborne dispersions, solution, emulsions and latex particles made from the alpha, beta-unsaturated organosilicon compounds of the present subject matter can be used as ingredients in personal care formulations including skin care, hair care, and nail care, such as lipsticks, mascaras, foundations, lotions, creams, shampoos, conditioners and nail polishes, to improve their ware, tactile properties and ease of application. The homopolymer, copolymer, emulsion, waterborne dispersion, solution and latex particles made from the alpha, beta-unsaturated organosilicon compounds of the present subject matter can be used in textile and fiber treatment applications to impart smooth, soft feel and wettability to both natural and synthetic fibers. Finally the homopolymer, copolymer, emulsion, waterborne dispersion, solution and latex particles can be incorporated into coating formulations for metal, plastic, wood and paper, such as varnishes, latex paints and roofing compositions.

In another embodiment of the present subject matter, other specific used of alpha, beta-unsaturated organosilicon compounds of Formula (1) and copolymers made therefrom are as additives or resin for coatings and adhesives. Coatings containing the additive or copolymer of the present subject matter may show a number of superior properties, including lower surface energy, slip, soft feel, flow and leveling, water resistance and release properties. These properties are of particular interest in coatings for graphic, textile, plastic, wood, architectural, automotive, metal and pressure sensitive adhesive applications. The monofunctionality of the silicon-containing monomer containing a polymerizable alpha, beta-unsaturated amido group prevents excessive viscosity buildup during polymer synthesis. The coatings containing the novel alpha, beta-unsaturated organosilicon compounds of Formula (1) and copolymers made therefrom of the present subject matter may include powder coatings, conversion coatings, passivation coatings, primers, high solids coating, waterborne coatings, solventborne coatings, e-coatings, hardcoats and the like. The following Examples are illustrative only and should not be construed as limiting the subject matter. All parts and percentages are by weight and all temperatures are in degrees Celsius unless explicitly stated otherwise.

EXAMPLES

The silicone-hydrogel films are evaluated for lens properties using the following methods.

Equilibrium Water Content:

The film is immersed in buffer of pH 6.5-8.5 (chosen based on the ionic types) for 48 hours. Then the surface water is wiped off gently using lintless tissue paper. The hydrated film is weighed precisely and then dried in solid content analyzer at 150° C. for 15 minutes and weighed again for dry weight. Water content is calculated based on weight change using the following equation.

$$\% \text{ Water content} = \frac{[\text{Weight of hydrated lens} - \text{Weight of dry lens}] \times 100\%}{\text{Weight of hydrated lens}}$$

Water Wettability:

Water wettability is measured according to: Neumann A W, Godd R J. Techniques of measuring contact angles. In: Good R J, Stromberg R R, Editors. Surface and Colloid science—Experimental methods, vol. 11. New York: Plenum Publishing; (1979), pp. 31-61.

Water wettability of the film surface is evaluated by measuring contact angle using Tracker TECLIS goniometer. In a static contact angle method the wet film is first pressed with lintless tissue paper and then a drop of water is placed on the surface. The contact angle is measured using a goniometer. Lower contact angle values represent a greater degree of hydrophilicity or better surface wettability of the film.

Oxygen Permeability (Dk):

The oxygen permeability (Dk) for these samples was measured using polarographic technique following ISO 9913 standards method. The film is clamped into the permeation cell and the donor chamber is filled with oxygen saturated PBS (phosphate buffered saline). The concentration of oxygen in the receptor cell is monitored, and plotted as a function of time and the permeability is determined from the initial slope of the plot.

Oxygen permeability, also called the Dk value, which may be expressed in Barrer, wherein 1 Barrer=$10^{-11}$ (cm$^3$ O$_2$) cm cm$^{-2}$s$^{-1}$ mmHg$^{-1}$, wherein (cm$^3$ O$_2$) is at a quantity of oxygen at standard temperature and pressure and wherein cm represents the thickness of the material and cm$^{-2}$ is the reciprocal of the surface area of that material or $3.348 \times 10^{-19}$ kmol m/(m$^2$ s Pa). The Dk of water is 80 Barrer.

Modulus:

The Young's modulus of the hydrated film is measured using an Instron tensile tester. The wet samples are cut into 6 cm×0.8 cm strips and the mechanical properties are measured with a load cell of 50 N and crosshead speed of 10 mm/minute. The modulus is determined from the initial slope of a stress-strain curve. Modulus is directly correlated to the softness of the material. Lower the modulus, softer is the material.

Refractive Index:

The refractive index is measured in accordance with ASTM D1218, Standard Test Method for Refractive Index and Refractive Dispersions of Hydrocarbon Liquids, at 20° C.

Density:

The density is measured in accordance with ASTM D891-09, Method for Specific Gravity, Apparent, of Liquid Industrial Chemicals, at 20° C.

Examples 1-7

Example 1

Synthesis of 4-(2-(acryloyloxy)-4-(2-(1,1,1,3,5,5,5-heptamethyltrisiloxane-3-yl)ethyl)cyclohexyl)oxy-4-oxabutanoic acid A round-bottom flask equipped with a stirring bar, a reflux condenser and a dropping funnel was charged with vinyl cyclohexyl epoxy functionalized trisiloxane, 100 g and toluene, and the reaction mixture was heated to 70-75° C. At this point a catalytic amount of titanium isopropoxide and 2,2,6,6-Tetramethylpiperidine 1-oxyl was added and the reaction mixture was further heated to 90° C. 21 g of acrylic acid was added gradually to the reaction mixture. After completion, the reaction mixture was passed over Dowex-WBA resin to remove unreacted acrylic acid. The product was decolorized using activated charcoal and filtered over celite bed. The filtrate was vacuum stripped to yield a pale yellow color product, 5-(2-(1,1,1,3,5,5,5,-heptamethyltrisiloxane-3-yl)ethyl)-2-hydroxycyclohexylacrylate.

50 g of 5-(2-(1,1,1,3,5,5,5,-heptamethyltrisiloxane-3-yl)ethyl)-2-hydroxycyclohexylacrylate and 18 g of toluene and succinic anhydride are further charged into a round bottom flask equipped with a stirring bar, a reflux condenser, and nitrogen inlet. To this, triethylamine and hydroquinone are added as a catalyst and radical scavenger, respectively, and the reaction mixture was heated to 60-65° C. After completion, the product was vacuum striped, re-dissolved in chloroform, and washed with brine solution. The organic phase was passed over Tulsion T66-MP resin to remove traces of triethylamine and decolorized using activated charcoal. The organic layer was concentrated after removal of the charcoal to yield a pale yellow, viscous product.

Example 2

Synthesis of (4-(((2-(acryloyloxy)-5-(2-(1,1,1,3,5,5,5-heptamethyltrisiloxan-3-yl)ethyl)cyclohexyl)oxy)-4-oxobut-2-enoic acid 50 g of 5-(2-(1,1,1,3,5,5,5,-heptamethyltrisiloxane-3-yl)ethyl)-2-hydroxycyclohexylacrylate and 18 g of toluene and maleic anhydride are further charged into a round bottom flask equipped with a stirring bar, a reflux condenser, and nitrogen inlet. To this, triethylamine and hydroquinone are added as a catalyst and radical scavenger, respectively, and the reaction mixture is heated to 60-65° C. After completion, the product was vacuum striped, re-dissolved in chloroform, and washed with brine solution. The organic phase was passed over Tulsion T66-MP resin to remove traces of triethylamine and decolorized using activated charcoal. The organic layer was concentrated after removal of the charcoal to yield a pale yellow, viscous product.

Example 3

Synthesis of 3-(((2-(acryloyloxy)-5-(2-(1,1,1,3,5,5,5-heptamethyltrisiloxan-3-yl)ethyl)cyclohexyl)oxy)carbonyl)but-3-enoic acid A round bottom flask equipped with a stir bar, reflux condenser and nitrogen inlet was charged with 50 g of 5-(2-(1,1,1,3,5,5,5,-heptamethyltrisiloxane-3-yl)ethyl)-2-hydroxycyclohexylacrylate and toluene. To this, triethylamine and hydroquinone are added as a catalyst and radical scavenger, respectively, and the reaction mixture is heated to 60-65° C. To this, 20 g of itaconic anhydride was added gradually. After completion, the product was vacuum striped, re-dissolved in chloroform, and washed with brine solution. The organic phase was passed over Tulsion T66-MP resin to remove traces of triethylamine and decolorized using activated charcoal. The organic layer was concentrated after removal of charcoal to yield a pale yellow, viscous product.

Example 4

Synthesis of 4-((5-(2-(1,1,1,3,5,5,5-heptamethyltrisiloxan-3-yl)ethyl)-2-(2-methacrylamidoacetoxy)cyclohexyl)oxy)-4-oxobutanoic acid A round-bottom flask equipped with a stirring bar, reflux condenser, and dropping funnel was charged with 25 g of vinyl cyclohexyl epoxy functionalized trisiloxane, Methyl ethyl ketone, and TEMPO (2,2,6,6-Tetramethylpiperidine 1-oxyl) and the reaction mixture was heated to 75-80° C. At this point, a pinch of glycine methacrylate and a catalytic amount of titanium isopropoxide was added, and the reaction mixture was further heated to 80° C. To this reaction mixture, 10 g of glycine methacrylate was added gradually. After completion, the product was isolated, re-dissolved in ethyl acetate, and the organic layer was washed with brine. The organic layer was concentrated to yield a pale yellow product, 4-(2-(1,1,1,3,5,5,5-heptamethyltrisiloxan-3-yl)ethyl)-2-hydroxycyclohexyl 2-methacrylamidoacetate.

15 g of 4-(2-(1,1,1,3,5,5,5-heptamethyltrisiloxan-3-yl)ethyl)-2-hydroxycyclohexyl 2-methacrylamidoacetate and 4.6 g of toluene and succinic anhydride are further charged into a round bottom flask equipped with a stirring bar, a reflux condenser, and nitrogen inlet. To this, triethylamine and hydroquinone are added as a catalyst and radical scavenger, respectively, and the reaction mixture is heated to 60-65° C. After completion, the product was vacuum striped, re-dissolved in chloroform, and washed with brine solution. The organic phase was passed over Tulsion T66-MP resin to remove traces of triethylamine and decolorized using activated charcoal. The organic layer was concentrated after removal of the charcoal to yield a pale yellow, viscous product.

Example 5

Synthesis of bis(4-((2-(acryloyloxy)-4-ethylcyclohexyl)oxy)-4-oxobutanoic acid) functionalized polydimethylsiloxane A round-bottom flask equipped with a stirring bar, a reflux condenser and a dropping funnel was charged with 15 g of 4-vinyl-1-cyclohexene 1,2-epoxide, and was heated to 70-75° C. At this point a catalytic amount of platinum(0)-1,3-divinyl-1,1,3,3-tetramethyldisiloxane complex solution in xylene, Pt ~2%, was added and the reaction mixture was further heated to 90° C. To this reaction mixture, 100 g of bishydride functionalized polydimethylsiloxane was added drop-wise. After completion of the reaction, the reaction mixture was cooled down to 70-75° C. and 100 mL of toluene, and a catalytic amount of titanium isopropoxide and TEMPO (2,2,6,6-Tetramethylpiperidine 1-oxyl) was added, and the reaction mixture was further heated to 90-95° C. To this reaction mixture, 9.5 g of acrylic acid, was added drop-wise over a period of two hours. The reaction was monitored using $^1$H-NMR spectroscopy. After completion of the reaction, the mixture was cooled down to 75° C. and 13 g of succinic anhydride, 14 g of Triethylamine, and 300 ppm of hydroquinone was added. The reaction was monitored using $^1$H-NMR spectroscopy. After completion the product was vacuum striped, re-dissolved in dichloromethane and washed with hot brine solution. The organic phase was passed over Tulsion T66-MP resin to remove traces of Triethylamine and decolorized using activated charcoal. The organic layer was filtered over Celite column to remove charcoal and then stirred along with Dowex WBA resin to remove traces of acrylic acid. The organic phase was further filtered and concentrated to yield pale yellow color viscous product.

Example 6

Synthesis of 4-((2-(acryloyloxy)-4-ethylcyclohexyl)oxy)-4-oxobutanoic acid functionalized polydimethylsiloxane A round-bottom flask equipped with a stirring bar, a reflux condenser and a dropping funnel was charged with 1.6 g of 4-vinyl-1-cyclohexene 1,2-epoxide, and was heated to 70-75° C. At this point catalytic amount of platinum(0)-1,3-divinyl-1,1,3,3-tetramethyldisiloxane complex solution in xylene, (Pt around 2%) was added and the reaction mixture was further heated to 90° C. To this reaction mixture, 10 g of monohydride functionalized polydimethylsiloxane, was added drop-wise. After completion of reaction, the reaction mixture was cooled down to 70-75° C. and 20 mL of Toluene, and a catalytic amount of Titanium isopropoxide and TEMPO (2,2,6,6-Tetramethylpiperidine 1-oxyl) was added and the reaction mixture was further heated to 90-95° C. To this reaction mixture, 1.7 g of acrylic acid, was added drop-wise over a period of two hours. The reaction was monitored using $^1$H-NMR spectroscopy. After completion of reaction, the reaction mixture was cooled down again to 75° C. and 2.5 g of succinic anhydride, 2.5 g of triethylamine, and 300 ppm of hydroquinone was added. The reaction was monitored using $^1$H-NMR spectroscopy. After completion the product was vacuum striped, re-dissolved in dichloromethane and washed with hot brine solution. The organic phase was passed over Tulsion T66-MP resin to remove traces of triethylamine and decolorized using activated charcoal. The organic layer was filtered over Celite column to remove charcoal and then stirred along with Dowex WBA resin to remove traces of acrylic acid. The organic phase was further filtered and concentrated to yield pale yellow color viscous product.

Example 7

Synthesis of 4-((2-(acryloyloxy)-4-ethylcyclohexyl)oxy)-4-oxobutanoic acid functionalized Polysilsequioxane (POSS)

A round-bottom flask equipped with a stirring bar, a reflux condenser and a dropping funnel was charged with 20 g of epoxycyclohexylisobutyl POSS and 40 g of toluene. The reaction mixture was heated to 70-75° C. and a catalytic amount of titanium isopropoxide and TEMPO (2,2,6,6-Tetramethylpiperidine 1-oxyl) was added. The reaction mixture was further heated to 90-95° C., and 3.4 g of acrylic acid was added drop-wise. The reaction was monitored using $^1$H-NMR spectroscopy. After completion of reaction, the reaction mixture was cooled to 70-75° C. and 2.7 g of succinic anhydride, 2.6 g of triethylamine, and 300 ppm of hydroquinone, was added.

The reaction was monitored using $^1$H-NMR spectroscopy. After completion, the final product was vacuum striped, re-dissolved in dichloromethane and washed with hot brine solution. The organic phase was passed over Tulsion T66-MP resin to remove traces of Triethylamine and decolorized using activated charcoal. The organic layer was filtered over celite column to remove charcoal and then stirred along with Dowex WBA resin to remove traces of acrylic acid. The organic phase was further filtered and concentrated to yield pale yellow color viscous product.

Examples of Hydrogel Films:

Selected hydrogel films are prepared using monomers described in Examples 1 to 7 formulated along with other organic monomers such as 2-hydroxyethyl methacrylate (HEMA), N,N-dimethyl acrylamide (DMA), N-vinylpyrrolidone (NVP) and crosslinkers such as ethylendeglycol dimethacrylate (EGDMA) or ABA type siloxane (containing about 45-52 dimethylsilyloxy units) polyether (a total of about 22 EO units) dimethacrylate macromer described earlier (Ref WO2013/142062). Other additives used in the formulations are polyvinylpyrrolidone (PVP). The films are cured using 2-hydroxy-2-methyl propiophenone as radical initiator (0.5 wt. %). The resultant clear, homogeneous solution is poured into PET (poly(ethylene terephthalate)) to a measuring gap of 1 mm. The formulations are cured by exposure to UV irradiation of 105 mW/cm² for 20-60 seconds. The films are evaluated for equilibrium water content, water wettability, oxygen permeability and modulus as listed in Table 1.

TABLE 1

Hydrogel formulation and characterization data

| Constituents (Wt. %) | Film 1 | Film 2 | Film 3 | Film 4 | Film 5 | Film 6 | Film 7 | Film 8 | Film 9 | Film 10 |
| --- | --- | --- | --- | --- | --- | --- | --- | --- | --- | --- |
| Example 1 | 49.5 | 49.5 | 69 | 69 | 49.8 | | 49.8 | | 37.1 | |
| Example 5 | | | | | | 49.8 | | 19.9 | | |
| Example 6 | | | | | | | | 49.8 | 37.1 | |
| Example 7 | | | | | | | | | | 24.6 |
| NVP | 4.95 | 24.8 | | | | | | | | |
| DMA | 19.8 | 24.8 | 29.5 | 26.6 | 29.8 | 49.8 | 29.8 | 29.8 | 24.8 | 49.2 |
| HEMA | 24.8 | | | | | | | | | |
| PVP | | | | | 2.9 | | | | | |
| ABA-D45 Siloxane Macromer | | | | | | 19.9 | | | | |
| EGDMA | 0.49 | 0.49 | 0.98 | 0.98 | | | | | 0.49 | 0.98 |
| UV initiator | 0.49 | 0.49 | 0.49 | 0.49 | 0.49 | 0.49 | 0.49 | 0.49 | 0.49 | 0.49 |
| 2-propanol | | | | | | | | | | 24.6 |
| Optical Appearance | Clear | Clear | Clear | Clear | Clear | Clear | Clear | Clear | Clear | Clear |
| Modulus (MPa) | 0.4 | 0.9 | 0.9 | 0.6 | 0.7 | 1.8 | 1.6 | 1.3 | 1.2 | 2.0 |
| Water content (wt. %) | 25 | 66 | 65 | 62 | 56 | 56 | 54 | 45 | 56 | 78 |
| Contact Angle (Deg) | 45 | 15 | 20 | 30 | 20 | 58 | 54 | 50 | 35 | 40 |

These alpha, beta-unsaturated organosilicon compounds are useful for making polymers and water-absorbing, oxygen-permeable silicone-hydrogel films containing the same that can be fashioned into biomedical devices, especially extended wear soft contact lenses.

While the above description contains many specifics, these specifics should not be construed as limitations on the scope of the subject matter, but merely as exemplifications of preferred embodiments thereof. Those skilled in the art will envision many other possible variations that are within the scope and spirit of the subject matter as defined by the claims appended hereto.

What is claimed is:

1. A composition comprising an alpha, beta-unsaturated organosilicon compound having the structure of Formula (1):

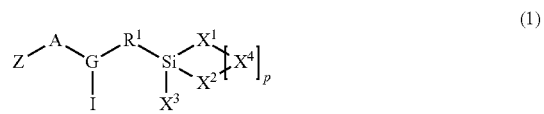

wherein:

$X^1$ is independently selected from linear or branched alkyl group containing 1-16 carbon atoms, trimethoxy silyl, trimethylsilyloxy, —O[Si(CH$_3$)$_2$O—]$_n$ wherein n is an integer chosen from 1 to 9, (CH$_3$)$_3$Si(CH$_2$)$_o$CH$_2$— wherein o is an integer from 0-3, (CH$_3$)$_3$SiCH$_2$CH$_2$Si(CH$_3$)$_2$O—, or (CH$_3$)$_3$Si(CH$_2$CH$_2$Si(CH$_3$)$_2$O)$_q$ wherein q is an integer chosen from 0-200; and, if $X^1$ is a monovalent radical, p is 0;

$X^2$ is independently selected from linear or branched alkyl group containing 1-16 carbon atoms, trimethoxy silyl, trimethylsilyloxy, —O[Si(CH$_3$)$_2$O—]$_n$ wherein n is an integer chosen from 1 to 9, (CH$_3$)$_3$Si(CH$_2$)$_o$CH$_2$— wherein o is an integer from 0-3, (CH$_3$)$_3$SiCH$_2$CH$_2$Si(CH$_3$)$_2$O—, or (CH$_3$)$_3$Si(CH$_2$CH$_2$Si(CH$_3$)$_2$O)$_q$— wherein q is an integer chosen from 0-200, or —[OSi(CH$_3$)$_2$]$_m$G$^1$, wherein G$^1$ is (CH$_3$)$_3$SiO—, or a reactive or non reactive silicone group with the general Formula (2a) or (2b):

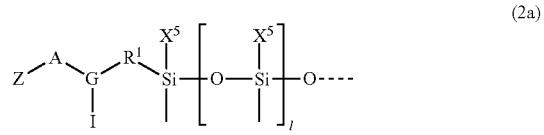

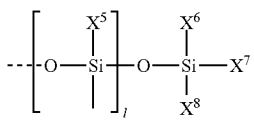
(2b)

where l is an integer chosen from 0-200; and p in Formula 1 is 0 when $X^2$ is of the Formula (2a), Formula (2b), or a monovalent radical;

$X^6$, $X^7$, and $X^8$ are independently chosen from a linear or branched alkyl group containing 1-16 carbon atoms, alkoxy, trimethylsilyloxy, or —O[Si(CH$_3$)$_2$O—]$_n$, wherein n is an integer chosen from 1 to 9, and wherein $X^6$ and $X^7$, $X^7$ and $X^8$, or $X^6$ and $X^8$ may form a ring;

$X^3$ and $X^5$ are independently chosen from methyl, butyl, trimethylsiloxy, (CH$_3$)$_3$SiCH$_2$CH$_2$—, (CH$_3$)$_3$SiCH$_2$CH$_2$Si(CH$_3$)$_2$O— or —OSi(CH$_3$)$_2$—, with the provisos that (i) when $X^1$ or $X^6$ is —O[Si(CH$_3$)$_2$O—]$_n$, then at least one of $X^3$ or $X^5$ is —OSi(CH$_3$)$_2$— and $X^1$ forms a chemical bond with the $X^3$ and/or $X^5$ forms a chemical bond with $X^6$ to correspondingly form a divalent —$X^1$-$X^3$— or $X^5$—$X^6$— group, which is bonded to the silicon atom to form a cyclic polysiloxane ring, and (ii) when $X^3$ and/or $X^5$ is —O[Si(CH$_3$)$_2$O—]$_n$ then $X^1$ and/or $X^6$ is —OSi(CH$_3$)$_2$— and the corresponding $X^1$ forms a chemical bond with the $X^3$ and/or $X^5$ forms a chemical bond with $X^6$ to form a divalent —$X^1$-$X^3$— or $X^5$-$X^6$— group, which is bonded to the silicon atom to form a cyclic polysiloxane ring; or $X^1$, $X^2$, and $X^3$ optionally are each —O[Si(R$^{16}$)O$_{3/2}$—]$_n$ and interconnected to form a polysilsequioxane ring as described in formula (2c)

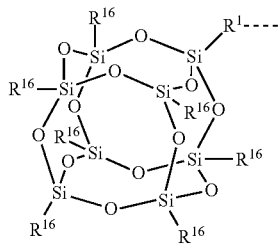
(2c)

wherein $R^{16}$ is independently chosen from a linear or branched alkyl or aralkyl group;

$X^4$ is an optional connecting group selected independently from dimethylsiloxy, —O[Si(CH$_3$)$_2$O—], or —CH$_2$CH$_2$(CH$_3$)$_2$SiO—, p is an integer chosen from 0-5;

$R^1$ is chosen from a chemical bond or an alkylene group containing from 1 to 16 carbon atoms and optionally containing a heteroatom of oxygen, sulfur and/or nitrogen;

G is a bridging unit between the siloxane moiety and reactive moiety independently selected from a linear or branched alkyl group or a carbocyclic group, the G unit optionally containing one or more heteroatoms;

A is a heteroatom;

I is a hydrophilic moiety with 0-100 carbon atoms which may contain heteroatoms;

Z is a polymerizable group of Formula (3):

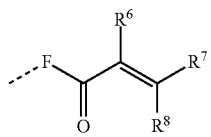
(3)

wherein $R^6$, $R^7$, and $R^8$ are independently selected from hydrogen or monovalent hydrocarbon radical with 1-5 carbon atoms; and F is an optional linker group chosen from aliphatic, cycloaliphatic, or aromatic hydrocarbon radical of 1 to about 16 carbons and optionally contains heteroatoms, with the proviso that if F is not utilized, then A is directly linked to the carbonyl group in Formula (3).

2. The composition of claim 1, wherein G is a branched alkyl moiety with the general formula (4a)

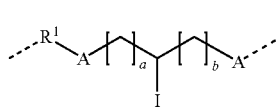
(4a)

wherein a is 0-16 and b is 1.

3. The composition of claim 1, wherein G comprises a saturated carbocyclic unit comprising 5 to 10 carbon atoms, having the general formula:

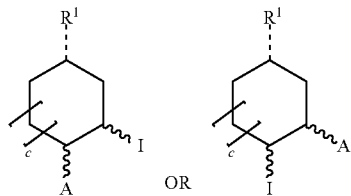

wherein c=0-5.

4. The composition of claim 3, wherein G is chosen from a positional isomer of the formula:

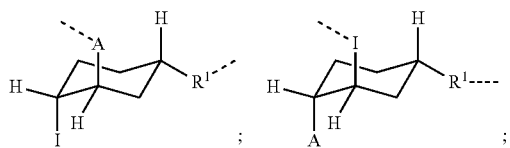

or a combination of two or more thereof.

5. The composition of claim 3, wherein G is chosen from:

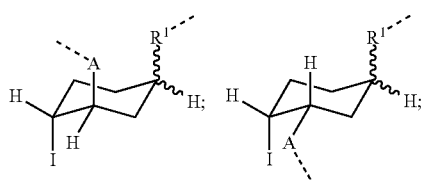

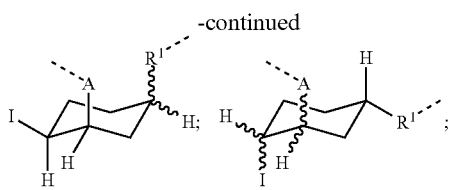

or a combination of two or more thereof.

6. The composition of claim 1, wherein $R^1$ is a divalent radical having a structure of Formula (5):

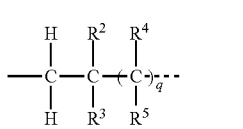

wherein $R^3$, $R^4$, and $R^5$ are independently selected from hydrogen, a linear, branched and/or cyclic hydrocarbon radical with 1 to 10 carbon atoms, and one or more of optionally contains heteroatoms; a $R^2$ is a hydrocarbon radical with 1 to 5 carbon atoms; and q is an integer chosen from 0 to 10.

7. The composition of claim 1, wherein I is a hydrophilic moiety having a structure of Formula (6):

—K-L-M  (6)

wherein:
 K is a divalent heteroatom or an oxygen;
 L is chosen from a divalent hydrocarbon radical chosen from a substituted or unsubstituted, linear or branched, aliphatic or aromatic hydrocarbon comprising 50 or fewer carbon atoms, which optionally contain heteroatoms and has a functionality chosen from an alcohol, an ether, an ester, an amide, an amine, a urea, a urethane, a cyano, a carbonate, a carbamate, a thiol, a thioether, thiol ester, or a combination of two or more thereof; and
 M is an ionic group chosen from —COOR, —NR$_2$, —PO(OR)$_2$, —OPO(OR)$_2$, —OSO$_3$H, —OH, where R is hydrogen or an alkyl group of from 1 to 3 carbon atoms, with the proviso that when L is a functionality that does not contain any carbon atoms then M cannot comprise any —NR$_2$, —OPO(OR)$_2$, —OSO$_3$H, or —OH groups.

8. The composition of claim 1, wherein F on the polymerizable group Z has a structure of the Formula (7):

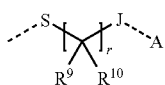

wherein:
 r is an integer selected from 0 to about 15;
 S is a divalent heteroatom independently selected from O, CH$_2$, NR$^{11}$, and sulfur;
 J is independently selected from a functional group chosen from —C(O)—, —NR$^{12}$C(O)—, —OC(O)—, —OS(O)—, and —P(O)OR$^{13}$—;
 $R^9$ and $R^{10}$ are independently chosen from a hydrocarbon radical with 1 to 5 carbon atoms; and
 $R^{11}$, $R^{12}$, and $R^{13}$ are independently selected from hydrogen or a monovalent hydrocarbon radical with 1-5 carbon atoms.

9. The composition of claim 1, wherein the alpha, beta-unsaturated compound has a structure of the formula:

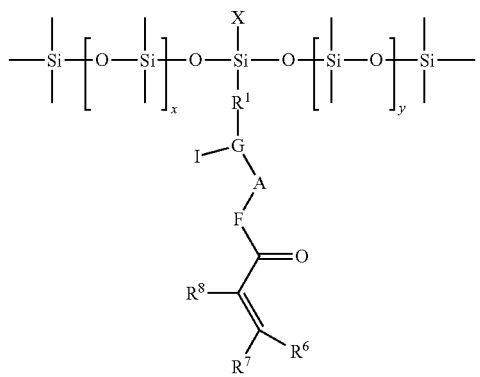

wherein:
 x and y are each integers chosen from 0-100;
 X is independently chosen from linear or branched alkyl group containing 1-16 carbon atoms, alkoxy, trimethoxysilyl, trimethylsilyloxy, (CH3)3Si[OSi(CH3)2]$_q$O— wherein q is an integer chosen from 0-100;
 $R^1$, $R^6$, $R^7$, $R^8$, $R^{16}$ are independently chosen from a linear or branched alkyl or aralkyl;
 G is chosen from a structure of the formula:

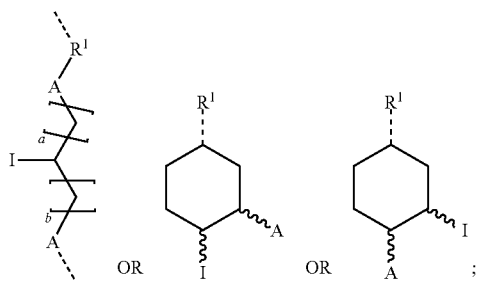

wherein a is 0-16 and b is 1
I is independently chosen from the following structures:

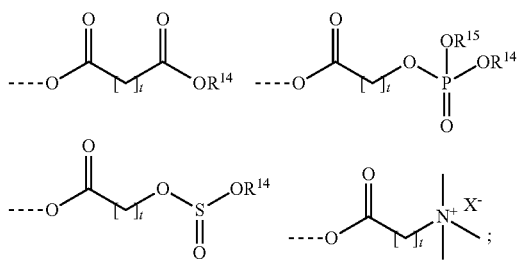

$R^{14}$ and $R^{15}$ are independently chosen from a hydrogen, linear or branched alkyl, aralkyl, or aromatic units with 1-20 carbon atoms, an alkali or alkaline earth metal anions, or a transition metal complex;
X— is independently selected from a halide, a carboxylate, a tosylate, a sulfonate, a phosphate, a phthalate, a phenolate, or an alkoxide, and;
t is an integer chosen from 1-16; and
A is an oxygen atom.

10. The composition of claim 1, wherein the alpha, beta-unsaturated compound has a structure of the formula:

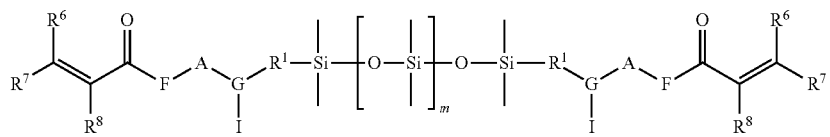

wherein:
m is an integer chosen from 0-200;
$R^1$, $R^6$, $R^7$, $R^8$ are independently chosen from a linear or branched alkyl or aralkyl;
G is chosen from the following structures:

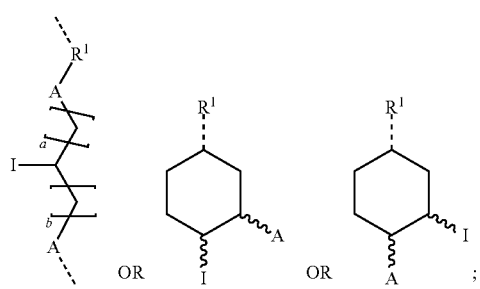

wherein a is 0-16 and b is 1
I is independently chosen from the following structures:

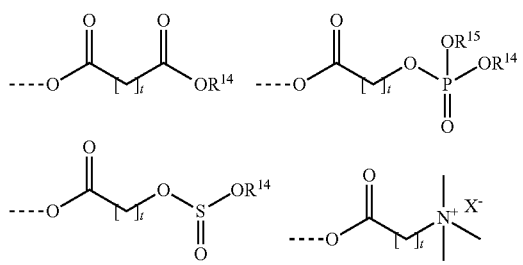

$R^{14}$ and $R^{15}$ are independently selected from hydrogen; a linear or branched alkyl, aralkyl, or aromatic linear or branched units with 1-20 carbon atoms, an alkali or alkaline earth metal anion or a transition metal complex;
X— is independently selected from a halide, a carboxylate, a tosylate, a sulfonate, a phosphate, a phthalate, a phenolate, and an alkoxide;
t is an integer chosen from 1-16;
A is an oxygen atom.

11. The composition of claim 1, wherein the alpha, beta-unsaturated compound has a structure of the formula:

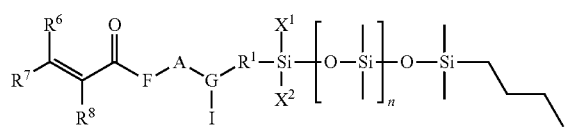

wherein:
n is an integer chosen from 0-200;
$R^1$, $R^6$, $R^7$, $R^8$ are independently selected from a linear or branched alkyl or aralkyl;

G is chosen from the following structures:

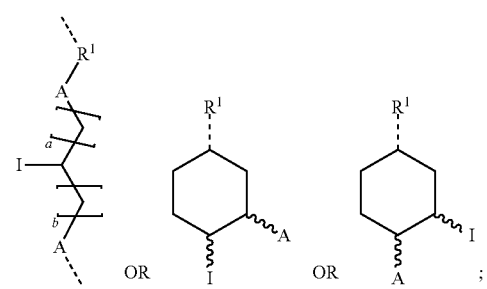

wherein a is 0-16 and b is 1
I is independently chosen from the following structures:

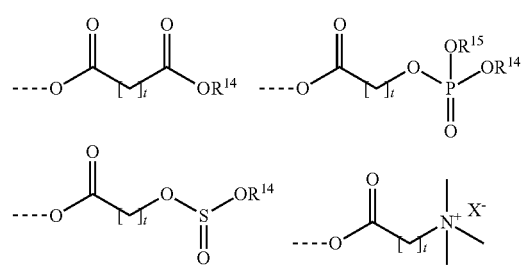

$R^{14}$ and $R^{15}$ are independently chosen from hydrogen; a linear alkyl, aralkyl, or aromatic linear or branched units with 1-20 carbon atoms, an alkali or alkaline earth metal anion and/or a transition metal complex;
X— is independently selected from a halide, a carboxylate, a tosylate, a sulfonate, a phosphate, a phthalate, a phenolate, and an alkoxide;
t is an integer chosen from 1-16; and
A is an oxygen atom.

12. The composition of claim 1, wherein the alpha, beta-unsaturated compound has a structure of the formula:

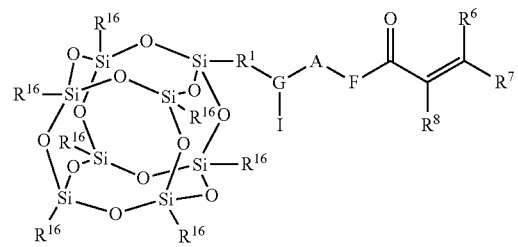

wherein:
$R^1$, $R^6$, $R^7$, $R^8$, $R^{16}$ are independently chosen from a linear or branched alkyl or aralkyl;

G is chosen from the following structures:

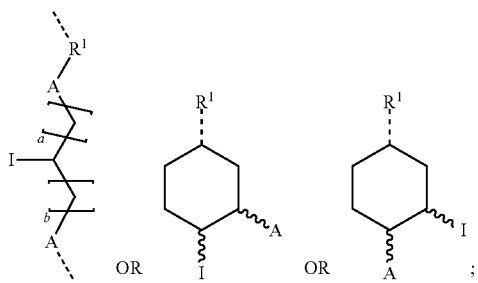

wherein a is 0-16 and b is 1
I is independently chosen from the following structures:

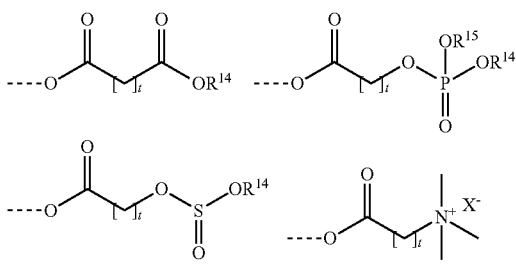

$R^{14}$ and $R^{15}$ are independently chosen from hydrogen; a linear or branched alkyl, aralkyl, or aromatic unit with 1-20 carbon atoms, an alkali or alkaline earth metal anion or a transition metal complex;

X— is independently selected from a halide, a carboxylate, a tosylate, a sulfonate, a phosphate, a phthalate, a phenolate, or an alkoxide;

t is an integer chosen from 1-16; and

A is an oxygen atom.

13. The composition of claim 1, wherein the composition is a copolymer comprising the organosilicon compound.

14. The composition of claim 13, wherein the copolymer is reactive or non-reactive.

15. The composition of claim 14, wherein the copolymer is a prepolymer.

16. The composition of claim 15, wherein the prepolymer is monofunctional or multifunctional.

17. The composition of claim 16, wherein the prepolymer is a (meth)acrylated reaction product of (1) the organosilicon compound, (2) a chain transfer agent, (3) one or more organic monomers, and (4) a radical initiator.

18. The composition of claim 17, wherein the chain transfer agent is chosen from 2-mercapto ethanol, 2-aminoethyl mercaptans, alkane thiols, thioglycolic acid and esters, bromotrichloromethane, 3-mercaptopropionic acid and esters, isooctyl 3-mercaptopropionate, Pentaerythritol tetrakis(3-mercaptopropionate), pentaerythritol tetrakis(3-mercaptopropionate), trimethylolpropane tris(3-mercaptopropionate), 4,4'-thiobisbenzenethiol, iodonitriles, etc.

19. The composition of claim 1, wherein the composition is a hydrogel.

20. The composition of claim 19, further comprising a free-radical polymerizable organic monomer, an initiator, and optionally a crosslinker.

21. The composition of claim 20, wherein the free-radical polymerizable organic monomer is chosen from a vinylic monomer, an acrylide monomer, an acrylic monomer, or a combination of two or more thereof.

22. The composition of claim 21, wherein the vinylic monomer is chosen from N-vinyl-pyrrolidone, N-vinyl-caprolactam, N-vinyl-acetamide, N-vinyl-formamide, N-vinyl-isopropylamide, vinyl benzene, vinyl naphthalene, vinyl pyridine, vinyl alcohol, vinyl containing silicone, or a combination of two or more thereof.

23. The composition of claim 21, wherein the acrylic monomer is chosen from 2-hydroxy-ethyl-methacrylate (HEMA), 2-hydroxy-ethyl-acrylate (HEA), hydroxyl propyl methacrylate, trimethylammonium 2-hydroxy propyl methacrylate hydrochloride, dimethylaminoethyl methacrylate, glycerol methacrylate, N,N-dimethylacrylamide, N-isopropylacrylamide, acrylamide, methacrylamide, acrylic acid, methacrylic acid, acrylated hydrophilic or hydrophobic organo-silicone, or a combination of two or more thereof.

24. The composition of claim 19, wherein a hydrophilic silicone macromer is present in an amount of from about 5 weight percent to about 50 weight percent of the hydrogel composition.

25. The composition of claim 24, wherein the ratio of a hydrophilic silicone macromer to a free-radical polymerizable organic monomer is from about 1:100 to about 100:1.

26. The composition of claim 24, wherein the ratio of a hydrophilic silicone macromer to a free-radical polymerizable organic monomer is from about 1:50 to about 50:1.

27. The l composition of claim 24, wherein the ratio of a hydrophilic silicone macromer to a free-radical polymerizable organic monomer is from about 1:10 to about 10:1.

28. The composition of claim 24, wherein the ratio of a hydrophilic silicone macromer to a free-radical polymerizable organic monomer is about 1:1.

29. The composition of claim 19, optionally comprising a cross-linker chosen from ethylene glycol dimethacrylate, trimethyloylpropane trimethacrylate, diethyleneglycol dimethacrylate, bisphenol A dimethacrylate, diglycidyl bisphenol A dimethacrylate, dimethacrylate-terminated polyethylene glycol, a reactive linear or pendant polyether modified silicone, or a combination of two or more thereof.

30. The composition of claim 19, wherein the composition comprises a thermal or a photo initiator chosen from 2,2'-azobis(2,4-dimethylpentanenitrile), 2,2'-azobis(2-methylpropanenitrile), 2,2'-azobis(2-methylbutanenitrile), peroxides such as benzoyl peroxide, benzoin methyl ether, diethoxyacetophenone, a benzoylphosphine oxide, 2-hydroxy-2-methyl propiophenone (HMPP), 1-hydroxycyclohexyl phenyl ketone, a Darocur type, an Irgacure type, or a combination of two or more thereof.

31. A contact lens comprising a hydrogel film formed from the composition of claim 19.

32. The composition according to claim 19, wherein the composition is a film forming additive in a textile, paper, leather, personal care, health care, home care, coating, painting or seed treatment formulations.

* * * * *